(12) United States Patent
McClellan et al.

(10) Patent No.: US 10,029,029 B2
(45) Date of Patent: Jul. 24, 2018

(54) APPARATUS AND METHOD FOR ELECTROSPINNING A NANOFIBER COATING ON SURFACES OF POORLY CONDUCTIVE THREE-DIMENSIONAL OBJECTS

(71) Applicants: Phillip McClellan, Akron, OH (US); William Landis, Akron, OH (US)

(72) Inventors: Phillip McClellan, Akron, OH (US); William Landis, Akron, OH (US)

(73) Assignee: The University of Akron, Akron, OH (US)

( * ) Notice: Subject to any disclaimer, the term of this patent is extended or adjusted under 35 U.S.C. 154(b) by 355 days.

(21) Appl. No.: 14/434,770

(22) PCT Filed: Oct. 18, 2013

(86) PCT No.: PCT/US2013/065611
§ 371 (c)(1),
(2) Date: Apr. 10, 2015

(87) PCT Pub. No.: WO2014/063013
PCT Pub. Date: Apr. 24, 2014

(65) Prior Publication Data
US 2015/0273110 A1    Oct. 1, 2015

Related U.S. Application Data

(60) Provisional application No. 61/715,502, filed on Oct. 18, 2012.

(51) Int. Cl.
*A61L 27/34*    (2006.01)
*D01D 5/00*    (2006.01)
*A61L 27/18*    (2006.01)

(52) U.S. Cl.
CPC ............ *A61L 27/34* (2013.01); *A61L 27/18* (2013.01); *D01D 5/0076* (2013.01); *D01D 5/0084* (2013.01); *A61L 2420/02* (2013.01)

(58) Field of Classification Search
CPC .............. A61L 2/00; B05C 13/00; B05D 1/04
(Continued)

(56) References Cited

U.S. PATENT DOCUMENTS

| 2007/0031607 | A1* | 2/2007 | Dubson ................. B05D 1/007 427/458 |
| 2010/0190254 | A1* | 7/2010 | Chian ................. A61L 27/3847 435/396 |
| 2010/0233115 | A1* | 9/2010 | Patel ...................... A61L 15/26 424/78.08 |

* cited by examiner

*Primary Examiner* — Dah-wei D Yuan
*Assistant Examiner* — Andrew Bowman
(74) *Attorney, Agent, or Firm* — Renner Kenner Greive Bobak Taylor & Weber

(57) ABSTRACT

The present invention is directed to a novel method and apparatus for facilitating and improving efficient application of nanofibers to the surface of poorly conductive three-dimensional objects using electrospinning. The apparatus and associated methods of the present invention provide a much more direct connection between the object and the grounded plate collector while allowing the object to be supported above the collector in a manner which promotes nanofiber deposition over the top, bottom and side surfaces of the object, closely covering all of its surfaces with nanofibers. Moreover, the deposition of electrospun nanofibers according to various embodiments of the present invention expands electrospinning technology to greater numbers of applications in which three-dimensional coatings of a wide nature are advantageous.

11 Claims, 6 Drawing Sheets

(58) Field of Classification Search
USPC .............. 427/2.24, 2.1, 458; 118/500, 621
See application file for complete search history.

APPARATUS AND METHOD FOR ELECTROSPINNING A NANOFIBER COATING ON SURFACES OF POORLY CONDUCTIVE THREE-DIMENSIONAL OBJECTS

CROSS REFERENCE TO RELATED APPLICATIONS

This application claims the benefit of U.S. provisional patent application Ser. No. 61/715,502 entitled "Design of a Novel Electrospinning Technique for Three-Dimensional Coating of Nanofibers on Surfaces of Non-Conductive Objects" filed Oct. 18, 2012 and International Application No. PCT/US2013/065611 entitled "Apparatus and Method for Electrospinning a Nanofiber Coating on Surfaces of Poorly Conductive Three-Dimensional Objects," which are incorporated herein by reference in their entirety.

FIELD OF THE INVENTION

The present invention is in the fields of electrospinning, and more particularly, in the area of covering three-dimensional objects with electrospun fibers, especially nanofibers.

BACKGROUND OF THE INVENTION

Electrospun nanofibers have been utilized in the field of tissue engineering for over a decade and the technology of electrospinning and the nanofibers themselves are advantageous for several reasons: nanofiber production through electrospinning is relatively simple, the mats generated by the nanofibers can closely resemble the three-dimensional structure of the extracellular matrix of certain tissues, and parameters of the electrospinning technique can be altered to yield a final product of specific structure and function. The latter is a unique quality of electrospinning and a principal factor in utilizing the method for tissue engineering applications.

Typically, a synthetic, biodegradable polymer, such as poly L-lactic acid (PLLA), polyglycolic acid (PGA), or polycaprolactone (PCL), is dissolved in an appropriate solvent to generate a moderately viscous solution which is suitable for electrospinning. The design of the collector for the electrospinning device can have a marked effect on the morphological characteristics of the nanofibrous mat produced. For instance, it is known that rotating collectors may be employed to obtain aligned nanofibers suitable for engineering nerve tissue. In most instances, however, the nanofibrous mat is collected onto a smooth surface, resulting in a thin, two-dimensional mat or "sheet" of nanofibers.

These two-dimensional mats of nanofibers have demonstrated notable benefits in repairing damage to tissues such as skin, which lack the need for a more complex, macroscopic three-dimensional structure. Much of the more recent research in tissue engineering with nanofibers has been focused primarily on the modification and manipulation of the fibers at the microscopic level. While these approaches identify various areas for potential improvement in the field of tissue engineering, they remain of limited utility in applications where macroscopic three-dimensional structures are required to regenerate larger tissues and organs.

Production of nanofibers for three-dimensional scaffolds has been more problematic. One approach for producing three-dimensional tubes of nanofibers which could be appropriate for tissue engineering blood vessels involves introducing a third dimension to the fibrous mat by rolling two dimensional nanofiber sheets into simple, hollow tubes. This approach has not been an effective method for producing tissue scaffolds of greater three-dimensional complexity. Others have fabricated heart valve prostheses from PCL using electrospinning. And while the trileaflet shape of the valve demonstrated a significant increase in overall three-dimensional complexity, the prosthesis remained relatively thin and this approach is unsuited to applications requiring increased thickness and strength of the scaffold.

Another approach known in the art is to produce nanofibers having overall three-dimensional structure resembling a cotton ball. Such scaffolds are known as Focused, Low density, and Uncompressed nanoFibrous (FLUF) mesh. These "cotton ball"-like FLUF scaffolds have a lower density of fibers when compared to flat nanofiber mats and have been found to provide a suitable three-dimensional environment for the infiltration and growth of INS-1 cells. However, these "cotton ball" scaffolds do not exhibit the necessary strength or structure for the engineering of other cells and tissues, such as those from bone and additional connective mineralized tissues. Yet another approach involves fabricating electrospun scaffolds using solutions of alginate and poly-ethylene oxide (PEO), which produce three-dimensional structures because of charge repulsion between individual fibers as a result of the negatively charged alginate. As with the FLUF scaffolds, however, the alginate-PEO scaffolds lack sufficient mechanical strength to be effective for engineering of harder tissues such as bone and other calcified tissues.

Recently, researchers have successfully designed and developed tissue-engineered bone in the shape of human digits (phalanges). Their engineered models consisted in part of the thin tissue (periosteum) covering the long bones from young calves. Periosteum was dissected and then wrapped and sutured about biodegradable polymer scaffolds composed of PCL/PLLA (75/25) and shaped like human digits. The periosteum/scaffold constructs were then implanted in athymic, immunodeficient mice (lacking the means for rejecting foreign tissue such as that from calves and other non-mouse species) for 20 and 40 weeks. Constructs retrieved from the mice at various time intervals of implantation and development demonstrated that bone tissue could be reproducibly regenerated in three dimensions by utilizing the periosteum as a viable source of bone progenitor cells. Further, it was found that the addition to constructs of certain growth factors, such as osteogenic protein-1 (OP-1) and basic fibroblast growth factor (bFGF), can expedite cell proliferation and differentiation. These molecules, applied directly to cells or provided to them through release and delivery vesicles or other means, have been shown to lead to more rapid formation of bone and other tissues.

In addition to such things as growth factor addition, the use of electrospun nanofibers has been shown to result in increased cell attachment and proliferation when compared to cells cultured in a monolayer environment. In this context, researchers have attempted to incorporate nanofibers into their experimental digit designs by wrapping the PCL/PLLA scaffolds with thin, pre-formed sheets of PGA nanofibers prior to application of periosteum. These experiments, however, have been largely unsuccessful because of the difficulty in maintaining direct contact at the interface between the nanofibers and the underlying PCL/PLLA scaffold. It has been found that without direct contact between the tissue scaffold and periosteum, the osteoprogenitor cells cannot infiltrate the scaffold and grow. Alternatively, suturing mats of nanofibers, rather than wrapping them, to the scaffolds as an alternate approach to direct contact is time-consuming and requires expertise to produce a suitable nanofiber-covered scaffold and subsequent construct. Additionally, as the complexity of the underlying construct increases, so does the number of sutures needed to ensure the nanofiber sheet remains in close contact with it.

A simple and novel method to circumvent the difficulties in designing an intimate contact between a nanofiber and scaffold is to apply nanofibers directly to the surface of the polymer scaffolds utilizing the electrospinning process. The surface to be coated needs only to be grounded, and thereby made electrically conductive, and placed in the path of the electrospun nanofibers as they are produced. Naturally conductive materials are easily coated, but poorly conductive materials, such as PCL/PLLA or other such polymers typically used for making polymer scaffolds have been found to be much more difficult to coat. Initial attempts to coat these polymer scaffolds by placing PCL/PLLA (75/25) scaffolds onto a flat, grounded electrical collector, directly in the path of the nanofiber jet were largely unsuccessful, resulting in only a few nanofibers being deposited onto the surface of the scaffolds.

What is needed in the art is a method and apparatus to facilitate and improve efficient application of nanofibers to the surface of other PCL/PLLA polymer scaffolds by providing a much more direct connection between the scaffold and the grounded plate collector while allowing the scaffold to be supported above the collector in a manner which promotes nanofiber deposition over the top and sides of the PCL/PLLA scaffold, closely covering the scaffold surfaces.

SUMMARY OF THE INVENTION

The present invention is directed to a novel method and apparatus for facilitating and improving efficient application of nanofibers to the surface of poorly conductive three-dimensional objects using electrospinning. The apparatus and associated methods of the present invention provide a much more direct connection between the object and the grounded plate collector while allowing the object to be supported above the collector in a manner which promotes nanofiber deposition over the top, bottom and side surfaces of the object, closely covering all of its surfaces with nanofibers. Moreover, the deposition of electrospun nanofibers according to various embodiments of the present invention expands electrospinning technology to greater numbers of applications in which three-dimensional coatings are advantageous.

In some embodiments of the apparatus and method of the present invention, a fine needle or another electrically conductive implement is inserted through a poorly conductive polymer scaffold such as PCL/PLLA and electrically connected to the grounded plate collector of the electrospinning apparatus to promote the collection and distribution of sufficient electric charge to attract charged nanofibers over the full, three-dimensional surface of the poorly conductive scaffold. The present invention is a vast improvement over comparable techniques for applying an electrospun coating to a poorly conductive object in three dimensions known in the art. It is believed that the needle or similar electrically conductive implement inserted through the object serves as a conductor of sufficient electric charge to attract charged nanofibers over the full surface complement of the object. The resulting electrospun nanofibers are in contact with the coated scaffold or other object such that they do not separate, delaminate or otherwise dissociate from the object surfaces when the coated structure is tested by immersion in 100% ethanol for 24 hours during a routine sterilization.

In a first embodiment, the present invention is directed to a method for coating an object in three dimensions with electrospun polymer nanofibers, comprising: (a) placing a three-dimensional object between a spinneret and a grounded collector, the spinneret holding a spinnable polymer fluid and the three-dimensional object having a first surface oriented toward the spinneret and a second surface oriented toward the grounded collector; (b) mounting the three-dimensional object on an electrically conductive supporter by passing it through the interior of the three-dimensional object such that a first end of the electrically conductive supporter extends through the first surface of the three-dimensional object and a second end of the electrically conductive supporter is electrically connecting to the grounded collector; and (c) applying a high voltage power to the spinneret thereby (d) generating electrospun polymer fibers of said spinnable polymer fluid that are attracted to said three-dimensional object and coat said three-dimensional object with electrospun polymer fibers in three dimensions.

In some embodiments, the present invention may include the method of the first embodiment, as set forth above further comprising providing a gap between the second surface of said three-dimensional object and said grounded collector, such that in said step (d) the electrospun polymer fibers coat the second surface of the three-dimensional object.

In some embodiments, the present invention may include any of the methods of the first embodiment, as set forth above wherein said step (b) includes mounting the three-dimensional object to at least a second electrically conductive supporter, said second electrically conductive supporter passing it through the interior of the three-dimensional object such that a first end of the second electrically conductive supporter extends through the first surface of the three-dimensional object and a second end of the second electrically conductive supporter is electrically connecting to the grounded collector.

In some embodiments, the present invention may include any of the methods of the first embodiment, as set forth above wherein the supporter has a higher conductivity than the three-dimensional object. In some embodiments, the present invention may include any of the methods of the first embodiment, as set forth above wherein the three-dimensional object is poorly conductive.

In some embodiments, the present invention may include any of the methods of the first embodiment, as set forth above wherein the three-dimensional object is a subcellular, cellular, tissue, or organ scaffold comprised of a polymer selected from the group consisting of biodegradable polyesters, polylactic acid, polycaprolactone, polyglycolic acid, and combinations thereof. In some embodiments, the present invention may include any of the methods of the first embodiment, as set forth above wherein said spinnable polymer fluid comprises a polymer selected from the group consisting of polylactic acid, polycaprolactone, polyglycolic acid, collagen, chitosan, fibrinogen, and combinations thereof.

In some embodiments, the present invention may include any of the methods of the first embodiment, as set forth above wherein said spinnable polymer fluid comprises poly L-lactic acid.

In some embodiments, the present invention may include any of the methods of the first embodiment, as set forth above wherein said electrically conductive supporter is comprised of a highly conductive material selected from the group consisting of stainless steel, titanium, copper, gold, silver aluminum, iron, and combinations thereof. In some embodiments, the present invention may include any of the methods of the first embodiment, as set forth above wherein said electrically conductive supporter is a stainless steel needle.

In some embodiments, the present invention may include any of the methods of the first embodiment, as set forth above further comprising after said step (d): e) inverting said three-dimensional object and said conductive supporter so that said second surface of said three-dimensional object and said second end of said electrically conductive supporter are oriented toward said spinneret and said first surface of said three-dimensional object and said first end of said electrically conductive supporter are oriented toward said grounded collector wherein there is a gap between the first surface of said three-dimensional object and said grounded collector to permit said electrospun polymer fibers to coat the first surface of said three-dimensional object; f) electrically connecting said first end of said electrically conductive supporter to said grounded collector; and g) applying a second high voltage power to said spinneret thereby generating electrospun polymer fibers of said spinnable polymer fluid that are attracted to said three-dimensional object and coat said three-dimensional object with electrospun polymer fibers in three dimensions.

In a second embodiment, the present invention is directed to a an apparatus for coating an object in three dimensions with electrospun polymer fibers, comprising: a spinneret; a DC power source; a grounded collector; an electrically conductive supporter having a first end oriented toward said spinneret and a second end oriented toward said grounded collector; and a three-dimensional object positioned between said spinneret and said grounded collector and having a first surface oriented toward said spinneret and a second surface oriented toward said grounded collector wherein the three-dimensional object is mounted on the electrically conductive supporter by passing the electrically conductive supporter through the interior of the three-dimensional object such that a first end of the electrically conductive supporter extends through the first surface of the three-dimensional object and a second end of the electrically conductive supporter is electrically connecting to the grounded collector on said electrically conductive supporter.

In some embodiments, the present invention may include any apparatus of the second embodiment, as set forth above, further comprising two or more electrically conductive supporters each electrically conductive supporter passing through the interior of the three-dimensional object such that a first end of each electrically conductive supporter extends through the first surface of the three-dimensional object and a second end of each electrically conductive supporter is electrically connecting to the grounded collector on said electrically conductive supporter.

In some embodiments, the present invention may include any apparatus of the second embodiment, as set forth above, wherein there is a gap between the second surface of said three-dimensional object and said grounded collector. In some embodiments, the present invention may include any apparatus of the second embodiment, as set forth above, wherein said electrospinning apparatus further comprising two or more spinnerets.

In some embodiments, the present invention may include any apparatus of the second embodiment, as set forth above, wherein said electrically conductive supporter has a higher conductivity than said three-dimensional object. In some embodiments, the present invention may include any apparatus of the second embodiment, as set forth above, wherein said three-dimensional object is poorly conductive.

In some embodiments, the present invention may include any apparatus of the second embodiment, as set forth above, wherein said three-dimensional object is a scaffold made of a polymer selected from the group consisting of biodegradable polyesters, polylactic acid, polycaprolactone, polyglycolic acid, and combinations thereof.

In some embodiments, the present invention may include any apparatus of the second embodiment, as set forth above, wherein said conductive supporter is comprised of a highly conductive material selected from the group consisting of stainless steel, titanium, copper, gold, silver, aluminum, iron and combinations thereof. In some embodiments, the present invention may include any apparatus of the second embodiment, as set forth above, wherein said conductive supporter is a stainless steel needle.

In a third embodiment, the present invention is directed to an apparatus for coating an object in three dimensions with electrospun polymer fibers, comprising: at least one reservoir containing at least one spinnable polymer fluid selected from the group consisting of polylactic acid, polycaprolactone, polyglycolic acid, collagen, chitosan, fibrinogen, and combinations thereof; a DC power source; one or more electrically conductive nozzles wherein each of said one or more electrically conductive nozzle is electrically connected to said DC power source and is in fluid communication with at least one reservoir; a grounded collector electrically connected to said DC power source and to at least one of said one or more electrically conductive nozzles; a three-dimensional object to be coated in three dimensions with electrospun polymer fibers positioned between said one or nozzles and said grounded collector and has a first surface oriented toward said one or nozzles and a second surface oriented toward said grounded collector; and one or more electrically conductive supporters having a first end oriented toward said nozzle and a second end oriented toward said grounded collector, wherein at least one of said one or more electrically conductive supporters is inserted through said three-dimensional object such that the first end of at least one of said one or more electrically conductive supporters extends through the first surface of said three-dimensional object and the second end of said at least one of said one or more electrically conductive supporters is electrically connected to said grounded collector and extends from said second surface of said three-dimensional object to said grounded collector to form a gap between the second surface of said three-dimensional object and said grounded collector to permit said electrospun fibers to coat the second surface of said three-dimensional object.

In some embodiments, the present invention may include any apparatus of the third embodiment, as set forth above, wherein said three-dimensional object is a subcellular, cellular, tissue, or organ scaffold made of a polymer selected from the group consisting of polylactic acid, polycaprolactone, polyglycolic acid, and combinations thereof. In some embodiments, the present invention may include any apparatus of the third embodiment, as set forth above, wherein said conductive supporter is a stainless steel needle.

In a fourth embodiment, the present invention is directed to an object coated in three dimensions with electrospun fibers prepared according to any of the methods of the first embodiment of the invention, as set forth above. In some embodiments, the present invention may include the object of the fourth embodiment, as set forth above, wherein said object is a subcellular, cellular, tissue, or organ scaffold made of a polymer selected from the group consisting of polylactic acid, polycaprolactone, polyglycolic acid, and combinations thereof. In some embodiments, the present invention may include the object of the fourth embodiment, as set forth above, wherein said electrospun fibers are formed from a spinnable polymer fluid comprising a polymer selected from the group consisting of polylactic acid, polycaprolactone, polyglycolic acid, collagen, chitosan, fibrinogen, and combinations thereof.

In some embodiments, the present invention may include the object of the fourth embodiment, as set forth above, wherein said electrospun fibers are substantially adhered to said object In some embodiments, the present invention may include the object of the fourth embodiment, as set forth above, wherein said electrospun fibers have a diameter of from 0.5 nm to about 50 µm. In some embodiments, the present invention may include the object of the fourth embodiment, as set forth above, wherein said object is poorly conductive.

In a fifth embodiment, the present invention is directed to a use of the object of the fourth embodiment, as set forth above, selected from the group biomedical applications, coating small mechanical or electrical components, filtration applications, and combinations thereof.

In some embodiments, the present invention may include the use of the fifth embodiment, as set forth above, wherein the biomedical application is tissue engineering. In some embodiments, the present invention may include the use of the fifth embodiment, as set forth above, wherein the biomedical application is tissue engineering of collagenous and non-collagenous tissues including, bone, cartilage, tendon, ligament, skin, and combinations thereof.

BRIEF DESCRIPTION OF THE DRAWINGS

For a more complete understanding of the features and advantages of the present invention, reference is now made to the detailed description of the invention along with the accompanying figures in which:

FIG. 6A depicts the top surface (A) (facing the electrospinning device) and two adjoining scaffold side surfaces (B and C). FIG. 6B depicts the bottom surface (F) and the two other adjoining side surfaces (D and E).

DETAILED DESCRIPTION OF THE ILLUSTRATIVE EMBODIMENTS

The present invention is directed to a novel method and apparatus for facilitating and improving efficient application of nanofibers to the surface of poorly conductive three-dimensional objects using electrospinning. As used herein, the term "nanofiber" generally refers to polymer fibers having diameters in the "nano" scale but may also include fibers as large as 50 µm. The apparatus and associated methods of the present invention provide a much more direct connection between the object and the grounded plate collector to attract charged nanofibers over the full surface complement of the object, while allowing the object to be supported above the collector in a manner which promotes nanofiber deposition over the top, bottom and side surfaces of the object, closely coveting all of its surfaces with nanofibers. The resulting electrospun nanofibers are in contact with the object such that they do not separate, delaminate or otherwise dissociate from the object surfaces, even when the coated structure is tested by immersion in 100% ethanol for 24 hours during a routine sterilization. Moreover, the deposition of electrospun nanofibers according to various embodiments of the present invention expands electrospinning technology to greater numbers of applications in which three-dimensional coatings of a wide nature are advantageous.

Figure 1:
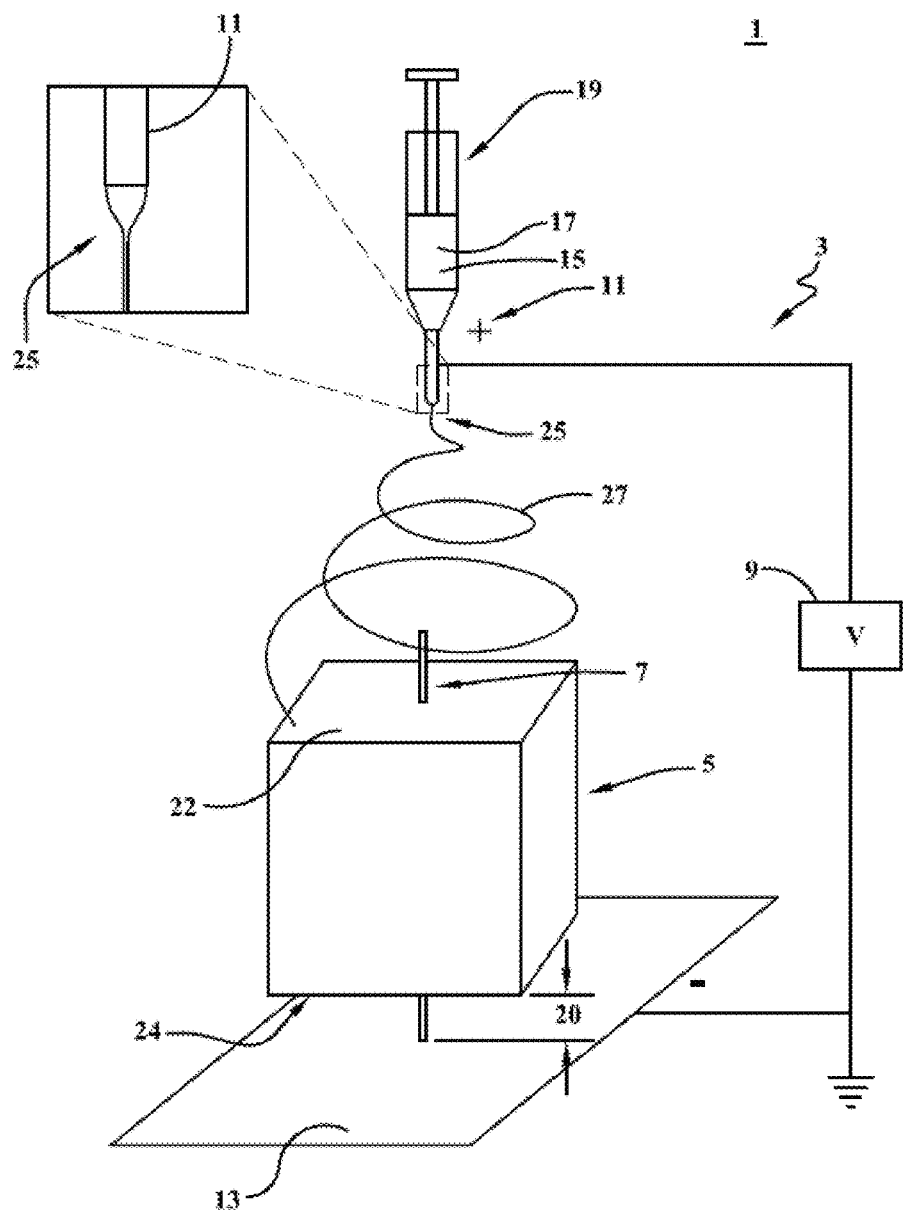
FIG. 1 is a schematic of an electrospinning apparatus for applying nanofibers to a three-dimensional object according to at least one embodiment of the present invention.

One aspect of the present invention is directed to an apparatus 1 for covering three-dimensional objects. FIG. 1 provides a general overview of at least one embodiment of the apparatus of the present invention. In basic outline, the apparatus 1 comprises an electrospinning device 3, a three-dimensional object 5, and one or more electrically conductive supporters 7. Suitable electrospinning devices are well known in the art and will be described herein only as needed to better understand the present invention. Electrospinning device 3 includes a power source 9, electrically connected to a spinneret 11 and a grounded collector 13. Spinneret 11 is in fluid communication with a fluid reservoir 15 containing a spinnable fluid 17.

As used herein, the terms "spinnable fluid," and/or "spinnable polymer fluid" refers to any fluid containing or comprising one or more polymers or other spinnable materials that can be mechanically formed into cylindrical or other long shapes by stretching and then solidifying the liquid or material. This solidification can occur by, for example, cooling, chemical reaction, coalescence, or removal of a solvent. Examples of spinnable fluids include polymer solutions, molten pitch, polymer melts, polymers that are precursors to ceramics, and molten glassy materials. "Spinnable fluids" are often comprised of one or more "spinnable materials" and one or more solvents. As those skilled in the art will appreciate, a variety of materials can be employed to make fibers including pure liquids, solutions of fibers, mixtures with small particles and biological polymers.

Any suitable spinnable fluid 17 may be used, including without limitation, a solution, spinnable mixture, or melt comprising a spinnable material including without limitation polylactic acid, polycaprolactone, polyglycolic acid, collagen, chitosan, fibrinogen, hyaluronan, polyethylene oxide, polyvinyl pyrrolidone, polyvinyl acetate, nylon, polyurethane, polybenzimidazole, polycarbonate, polyacrylonitrile, polyvinyal alcohol, polyethylene-co-vinyl acetate, polymethyl metacrylate, polyaniline, collagen, gelatin, silk-like polymer, polyvinylcarbazole, polyethylene terephtalate, polyacrilic acid, polystyrene, polyamide, polyninylchlororide, cellulose acetate, polyacrilamide, polyvinylidene fluoride, polyether imide, polyethylene, polypropylene, polyethylene naphtalate, mesophase pitch, polyacrylonitrile, coal tar, zirconium (IV) propoxide, titanium (IV) isopropoxide, yttrium nitrate hexahydrate, tetraethyl orthosilicate, zinc acetate, copper nitrate and/or combinations thereof. In some embodiments, the spinnable fluid 17 may contain one or more biodegradable polyester such as poly L-lactic acid, poly glycolic acid, polycaprolactone, or polybutylene terephthalate.

Suitable solvents for use in electrospinning are well known in the art and may include water, methanol, ethanol, isopropanol, n-butanol, acetone, chloroform, formic acid, dimethyl formamide, chloroform, dichloromethane, tetrahydrofuran, methylene chloride, methylethylketone, carbon disulfide, toluene, xylene, benzene, acetic acid, hexafluoro-2-propanol, and hexafluoroisopropanol, and/or combinations thereof. One of skill in the art will be able to determine suitable spinnable material (polymer)/solvent combinations without undue experimentation. In some embodiments, spinnable fluid 17 may contain PLLA and chloroform. In some embodiments, spinnable fluid 17 may contain collagen and hexafluoroisopropanol.

In addition, spinnable fluid 17 may contain one or more additives which may include without limitation pharmaceutically active compounds, cells, nanoparticles, colloids, small crystals, fluid droplets, trisilanol isobutyl polyhedral oligomeric silsesquinoxane (POSS) particles, soluble sol-gel precursors in that form into insoluble nanoparticles, inorganic pigments, small molecules capable of exhibiting therapeutic benefits, small molecules capable of exhibiting optical and electronic properties or stimuli responsive behavior, catalysts, catalytic precursors, cells, organelles, and biomolecules. In some embodiments, spinnable fluid 17 may contain β-tricalcium phosphate, apatite crystals, or silica nanoparticles.

In ordinary operation, the electrospinning device 3 forms nanofibers using the following procedure. The spinnable fluid 17 is brought from the reservoir 15 to the spinneret 11 at a set flow pressure and rate by means of one or more fluid pumps 19. Any suitable fluid pump 19 may be used and in some embodiments, the fluid pump 19 is a syringe pump. One of ordinary skill in the art will be able to select an appropriate flow pressure and/or flow rate to make suitable nanofibers 27 with out undue experimentation. A current is then applied system by the power source 9 creating an electrical potential between the spinneret 11 and the grounded collector 13 causing the spinnable fluid 17 to be drawn into a jet 25 and flow from the spinneret 11 toward the grounded collector 13. As it leaves the spinneret, the jet begins to elongate and as it does, it cools and/or the solvents in the spinnable fluid 17 evaporate, causing the jet to solidify into a nanofiber 27. Any additives in the spinnable fluid 17 may be incorporated into or otherwise encapsulated within nanofibers 27.

Nanofiber 27 need not be and often is not fully dry when it reaches the three-dimensional object 5. As one of ordinary skill in the art will appreciate, the degree to which the nanofibers 27 will still be "wet" when they reach the three-dimensional object 5 will depend upon the characteristics of the spinnable fluid 17 used. In some embodiments, for example, where the solvent used has a relatively slow rate of evaporation, such as chloroform, the nanofibers formed during the electrospinning process are still "wet" when they are deposited onto the surface of the three-dimensional object 5. In these embodiments, wetting allows some nanofibers to "melt" to the surface of the three-dimensional object 5 and to each other in the locations where they cross, increasing adhesion and contact between the nanofibrous coating and the three-dimensional object 5. In these embodiments, it appears that separation or dissociation between the nanofibers and the three-dimensional object 5 may be reduced or prevented, even when the coated objects were later placed in a liquid environment (for example, ethanol for sterilization or cell growth medium for cell culture).

Moreover, it should be appreciated that the electrospun nanofibers 27 should be small enough in diameter as to readily be moved by the electrical charge surrounding the three-dimensional object 5 to cover the surfaces of the three-dimensional object 5 not facing the spinneret 11. In some embodiments, nanofiber 27 may have a diameter of from 0.5 nm to about 50 μm. In some embodiments, nanofiber 27 may have a diameter of 10 nm to 100 nm. In some embodiments, nanofiber 27 may have a diameter of 500 nm to 10 μm.

Figure 3:
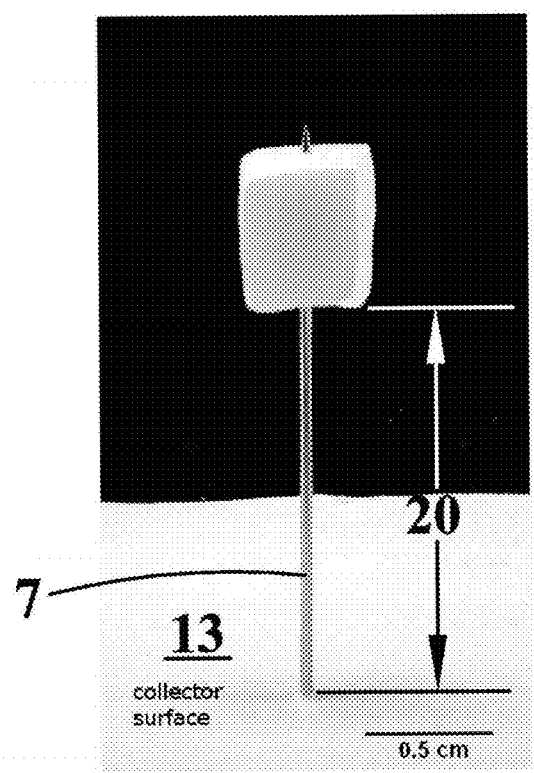
FIG. 3 is a photograph of a representative specimen of a PCL/PLLA scaffold mounted onto the end of the fine-point stainless steel needle according to at least one embodiment of the present invention. The fine point of the needle is shown protruding from the surface of the PCL/PLLA scaffold. The other end of the needle is connected to a flat, electrically grounded collector. Scale bar=0.5 cm

As can be seen in FIGS. 1 and 3, three-dimensional object 5 is positioned between spinneret 11 and grounded collector 13. As used herein, a "three-dimensional object" refers to any object or portion of an object having a measurable length, width and height and the term "coating in three dimensions" refers to the process of covering substantially all of the exposed surfaces with a coating of nanofibers. Three-dimensional object 5 can have any shape, but should be sized and oriented so that it may be coated with the nanofibers 27 as they are produced. Three-dimensional object 5 may be made from any suitable material, including without limitation, biodegradable polyesters, polylactic acid (PLA), PLLA, PGA, PCL, polybutylene terephthalate. In some embodiments, three-dimensional object 5 may be made from about 50% to about 90% PCL and from about 10% to about 50% PLLA. In some embodiments, three-dimensional object 5 may be made from about 75% PCL and about 25% PLLA In some embodiments, three-dimensional object 5 is a poor conductor of electricity.

In some embodiments, three-dimensional object 5 may be a subcellular, cellular, tissue, or organ scaffold made of a polymer such as PLA, PLLA, PCL and PGA and combinations thereof. In other embodiments, the three-dimensional object 5 may be a three-dimensional filter scaffold. In other embodiments, the three-dimensional object 5 may be a small mechanical or electrical component.

Figure 2:
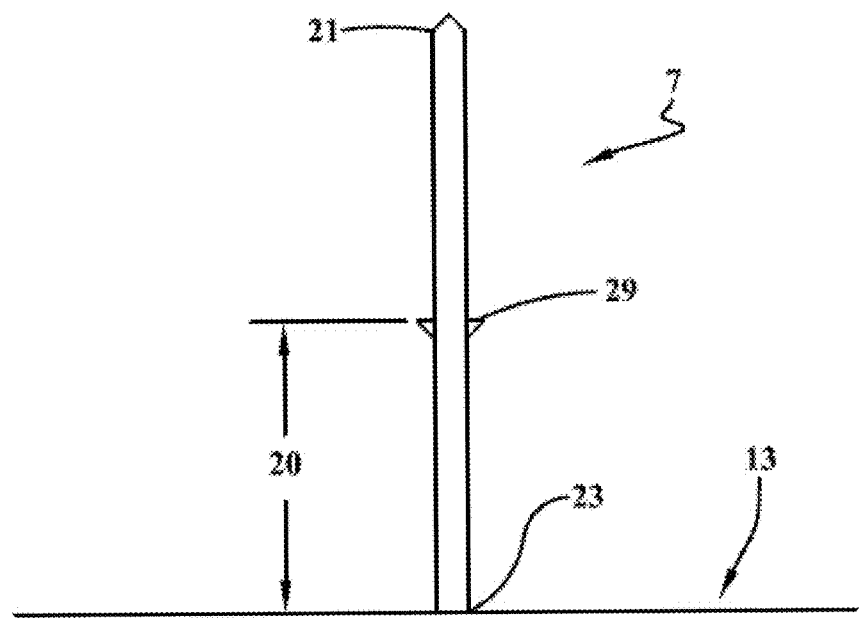
FIG. 2 is a front view of an electrically conductive supporter according to at least one embodiment of the present invention.

In reference to FIGS. 1-3, apparatus 1 further comprises at least one electrically conductive supporter 7. Each electrically conductive supporter 7 extends from the grounded collector 13 and through the three-dimensional object 5, holding it at a set distance from grounded collector 13. The gap 20 formed between the three-dimensional object 5 and the grounded collector 13 will have a distance d and must be large enough to permit the nanofibers to wrap around underneath three-dimensional object 5 to coat the surfaces of three-dimensional object 5 closest to the grounded collector 13 and furthest from the spinneret. The appropriate size of the gap 20 will vary depending upon a variety of factors including without limitation the size, shape and conductivity of the three-dimensional object 5, the size and composition of the nanofibers 27, the conductivity of the electrically conductive supporter 7, the voltage applied to form the nanofibers, and environmental conditions such as temperature and relative humidity.

The first end 21 of the electrically conductive supporter 7 extends out from a first surface 22 of three-dimensional object 5 facing spinneret 11. The second end 23 of electrically conductive supporter 7 extends from a second surface 24 of three-dimensional object 5 facing grounded collector 13 and is electrically connected thereto. The first end 21 of the electrically conductive supporter 7 provides an attractive electrical potential near the surface of the three-dimensional object 5 and also can provide an electrical connection to ions migrating on the surface of the polymer scaffold and/or collected nanofibers 27, thereby maintaining an attractive potential that collects more fibers.

The first end 21 of the electrically conductive supporter 7 may protrude any reasonable distance from the first surface 22 of three-dimensional object 5. It should be appreciated, however, that the portion of electrically conductive supporter 7 between the first surface 22 of three-dimensional object 5 and the spinneret will, by virtue of its proximity to the spinneret and electrical charge will attract and be coated with a significant number of fibers, fibers that will never reach the three-dimensional object 5. This may also result in a larger "peak" or tent-like web of fibers extending from the portion of the electrically conductive supporter 7 protruding from the electrically conductive supporter 7 and the first surface 22 of three-dimensional object 5, which may interfere with the fibers ability to adhere to the first surface 22 of three-dimensional object 5 properly. The optimal distance will depend upon a variety of factors including without limitation, the size, shape, and conductivity of three-dimensional object 5, the size and shape of the electrically conductive supporter 7 where it passes through the three-dimensional object 5, the voltage to be applied to generate the nanofibers, the cost, and the intended application of the final product. One of ordinary skill in the art will be able to identify an optimal protrusion distance for a particular application without undue experimentation. In some embodiments, first end 21 of the electrically conductive supporter 7 may protrude about 1mm from the first surface 22 of three-dimensional object 5. In some embodiments, first end 21 of the electrically conductive supporter 7 may protrude about 25 mm from the first surface 22 of three-dimensional object 5.

While, as discussed above, it is preferred that first end 21 extends out from the first surface 22 of three-dimensional object 5, the first end 21 may extend only to or just below the first surface 22 of three-dimensional object 5 in some embodiments, provided that electrically conductive supporter 7 can still provide an attractive electrical potential and an electrical connection to ions migrating on the surface of the polymer scaffold and/or collected nanofibers 27, as set forth above. In some embodiments, object 5 may be coated in three dimensions with electrospun fibers 27 such that the electrospun fibers 27 are substantially adhered to the three-dimensional object 5.

Electrically conductive supporter 7 can be made from any electrically conductive material including, but not limited to stainless steel, titanium, copper, gold, silver, aluminum, iron, and combinations thereof. In any event, the electrically conductive supporter 7 should be more conductive than the than the three-dimensional object 5 being coated with nanofibers 27. Other factors which may affect such a selection may include without limitation, the size, shape, and conductivity of three-dimensional object 5, the size and shape of the electrically conductive supporter 7 where it passes through the three-dimensional object 5, the voltage to be applied to generate the nanofibers, the cost, and the intended application of the final product.

In some applications, it is preferred that the diameter of the electrically conductive supporter 7 where it passes through the first and second surfaces 22, 24 of the three-dimensional object 5 be as small as possible in order to limit the size of the hole through the object being coated and the size of the "peak" of nanofibers that may form where the electrically conductive supporter 7 passes through the first and second surfaces 22, 24 of the three-dimensional object 5. As those of skill in the art will appreciate, where the electrically conductive supporter 7 is made from a more conductive the material, the diameter of the electrically conductive supporter 7 may be smaller. Further, where the three-dimensional object 5 is more conductive, less current may be required to ionize the surface of the three-dimensional object 5 and collected nanofibers 27, and maintain the attractive potential that collects more fibers. In that case, a somewhat less conductive (and likely less expensive) material may be used. Similarly, where a somewhat higher voltage is to be used by the electrospinning device 3, a somewhat less conductive material may be used for the electrically conductive supporter7 and conversely, where a somewhat lower voltage is be used to form the fibers, a somewhat more conductive material may be required. The optimal material will depend upon the particular application and those of ordinary skill in the art will be able to select a conductive material to be used to form the electrically conductive supporter 7 without undue experimentation. In some embodiments, electrically conductive supporter 7 is made from stainless steel.

Electrically conductive supporter 7 can be any shape provided that it: (1) is electrically connected to the grounded collector 13; (2) passes through the three-dimensional object 5 to be coated with nanofibers to extend through or to the first surface 22 of three-dimensional object; and (3) holds the three-dimensional object 5 at a sufficient distance from grounded collector 13 to allow the nanofibers to coat all of the surfaces of the three-dimensional object 5. As set forth above, the electrically conductive supporter 7 may also be altered with respect to its composition, density and size according to specific design requirements. For example, a longer electrically conductive supporter 7 would allow for mounting of longer objects, or an electrically conductive supporter 7 of larger diameter may be required to support heavier objects.

In some embodiments, electrically conductive supporter 7 may be a fine steel needle inserted by force through the three-dimensional object 5. In these embodiments, the three-dimensional object 5 in held in place on the electrically conductive supporter 7 by friction forces. In some other embodiments, the electrically conductive supporter 7 may be generally needle shaped as set forth above, and may also have stop 29 affixed to and/or integrated into to the electrically conductive supporter 7 at a distance d from the grounded collector 13 to keep the three-dimensional object 5 from sliding down the electrically conductive supporter 7 and getting too close to the grounded collector 13 and/or at a predetermined position on the electrically conductive supporter 7. (See FIG. 2)

Stop 29 may be any flange, ball, boss, ring, or any other item/structure affixed to and/or integrated into to the electrically conductive supporter 7 to keep the three-dimensional object 5 from sliding toward the grounded collector 13 and/or at a predetermined position on the electrically conductive supporter 7. In some embodiments, the portion of the electrically conductive supporter 7 running from the grounded collector 13 toward the spinneret 11 and covering at least the distance d may have a slightly larger diameter than the remainder of the electrically conductive supporter 7, again to keep the three-dimensional object 5 from sliding down the electrically conductive supporter 7 and getting too close to the grounded collector 13. In some embodiments, the second end 23 of electrically conductive supporter 7 may have a relatively broad diameter and gradually taper to a smaller diameter which passes through the three-dimensional object 5. In some embodiments, the stop 29 is positioned so that the portions of the electrically conductive supporter 7 running from the grounded collector 13 to the second surface of the three-dimensional object 5 and protruding from the first surface 22 of the three-dimensional object 5 are of equal length. In these embodiments, the electrically conductive supporter 7 may further comprise a second movable stop 31 (not pictured) to be inserted on the electrically conductive supporter 7 where it meets the first surface 22 of the three-dimensional object 5, to further hold three-dimensional object 5 in position on the electrically conductive supporter 7, even where the electrically conductive supporter 7 and three-dimensional object 5 are inverted.

Similarly, electrically conductive supporter 7 may have any suitable cross-sectional shape, including, for example, and without limitation, round, square, x-shaped, star-shaped, oblong, D-shaped, crescent shaped, triangular, or octagonal. Depending upon the intended application, electrically conductive supporter 7 may also include one or more conductive flanges, wings or other similar structures extending radially from the electrically conductive supporter 7 and into the interior of the object to better distribute the electrical charge over some types and/or shapes of objects. In some embodiments, the object may be designed having the holes already in place for the electrically conductive supporter 7.

Depending upon its shape and the configuration of the electrospinning device 3, the electrically conductive supporter 7 may be supported on or affixed to the grounded collector 13 in any manner known in the art, including without limitation friction fitting or screwing the electrically conductive supporter 7 into preformed (threaded) holes in the grounded collector 13; welding or soldering the electrically conductive supporter 7 to the grounded collector 13; and/or affixing the electrically conductive supporter 7 to a stand having a sufficiently broad base, that is electrically connected to the grounded collector 13. In some embodiments, the electrically conductive supporter 7 may be supported on or affixed to the grounded collector 13 by friction fitting it into preformed holes in the grounded collector 13.

Turning again to the three-dimensional object 5 as shown in FIGS. 1 and 3. As discussed above, the electrically conductive supporter 7 of the present invention passes through the three-dimensional object 5. Accordingly, the three-dimensional object 5 must be able to receive the electrically conductive supporter 7 (and permit it to pass through it), without being damaged in such a way as to render it unsuitable for the purpose for which it is intended. In embodiments where the three-dimensional object 5 is a pre-formed three-dimensional PCL/PLLA tissue scaffold, for example, it has been found that a fine stainless steel needle (the electrically conductive supporter 7) the may be forced through the scaffold without causing significant damage. In cases where the three-dimensional object 5 to be coated in nanofibers 27 is hard or brittle or in any case where it would be impossible or impractical to force the electrically conductive supporter 7 through the three-dimensional object 5 (i.e. the three-dimensional object 5 would break or be ruined or the electrically conductive supporter 7 is too soft), a passageway for the electrically conductive supporter 7 may be pre-formed in the three-dimensional object 5 by any appropriate method known in the art for that purpose.

The purpose of utilizing an electrically conductive supporter 7, such as a fine needle, in the electrospinning design is to promote the collection and distribution of sufficient electric charge to attract, by surface diffusion of ions, charged nanofibers over the full, three-dimensional surface of a poorly conductive object such as PCL/PLLA scaffold. If the needle, or another electrically conductive implement, is not used, then nanofibers are not deposited efficiently onto the entire surface of the object. Instead, it has been found that the nanofibers collect irregularly on the surface around or under the scaffold. Moreover, as set forth above, the arrangement of the object and needle, permits the object to be suspended above the flat collector such that the nanofibers are attracted to all of the sides of the object and not just to the sides directly exposed spinneret.

In most systems according to the present invention, the thicker the coating of fibers adhered to the three-dimensional object becomes, the fewer ions are able to migrate to the surface of the object to attract the fibers and at some point it can become difficult to add additional fibers to the object 5 as there are other equally or more electrically attractive places, like the grounded collector or a neighboring object. The thickness of the nanofiber coating that may be applied according to some embodiments of the present invention will depend upon such things as, without limitation, the size, shape, and conductivity of three-dimensional object 5, the size and shape of the electrically conductive supporter 7 where it passes through the three-dimensional object 5, the voltage to be applied to generate the nanofibers, and the proximity of other better grounded objects. In some embodiments, this effect can be moderated by slowly increasing the voltage applied to the system as the thickness of the nanofiber coating increases.

This method of the present invention is not limited to a single object size, shape, or composition. Larger objects of greater three-dimensional complexity may be coated with nanofibers in a fashion similar to that exemplified by the PCL/PLLA scaffolds described herein. Increasing the number of electrically conductive supporters 7 connecting the object to the grounded collector could allow for larger, irregular-shaped objects to be coated. In some embodiments, more than one electrically conductive supporter 7 may be utilized to attract the charged nanofibers in the case of very large or exceptionally complex three-dimensional structures.

However, care must be taken to prevent a web of nanofiber from forming between the first ends of the two or more electrically conductive supporters 7 used. If multiple electrically conductive supporters 7 are arranged too close together, whether to coat one or more than one object at a time, then a "bridge" of fibers can form which connects the multiple needles or objects with an eventual "web" of fibers. For the same reason that there needs to be enough distance between the grounded collector and the supported object so that the fibers are attracted to the under surfaces of the object as opposed to the grounded collector, if the electrically conductive supporters 7 are too close together, a substantial number of fibers may be attracted to the second electrically conductive supporter 7 rather than the other surfaces of the object to create a web of fibers between the two electrically conductive supporters 7.

Other modifications of the basic electrospinning process can be incorporated into methods of the present invention as well. For example, coaxial or emulsion techniques which have been utilized to sequester and deliver therapeutic could be used to produce a bioactive nanofiber coating on the surface of a scaffold in the shape of a specific organ (for example, a human ear, nose, finger, or femur). In some embodiments, multiple spinnerets may be used with the same, or in some cases, two or more different spinnable polymer fluids with similar and/or compatible electrical properties to produce two or more different types of nanofibers.

While the examples of rectangular-shaped scaffolds shown in FIGS. 1, 3-10 are coated on all their six surfaces, the thickness of the coating may not be uniform on each surface. The "peak" of nanofibers that collects on the end of the first end 21 of said electrically conductive supporter 7, for example, contributes to a thicker coating on the first surface 21 of the scaffold closest to the spinneret 11. Conversely, the nanofiber coating on the second surface 22 of the rectangular scaffold and opposite the spinneret 11 can be more sparse with portions of that surface 22 remaining relatively uncovered or lightly covered by fibers. Additional time of coating, however, can increase fiber coverage on this and the other surfaces. In some embodiments, more than one spinner may be used to produce multiple jets of nanofibers, reducing the time needed to coat the object. In some embodiments, more than one electrically conductive supporter 7 may be used with each one placed under a separate spinneret. Here again, care must taken to ensure that the electrically conductive supporters 7 are not too close together.

In some embodiments, moreover, after it has been coated with nanofibers as set forth above, the three-dimensional object 5 together with the electrically conductive supporter 7 may be inverted so that the second surface 24 of said three-dimensional object 5 and the second end 23 of the electrically conductive supporter 7 are oriented toward the spinneret 11 and the first end 21 of said electrically conductive supporter 7 is electrically connected to the grounded collector 13. As before, a gap 20 is provided between the first surface of the three-dimensional object 5 and the grounded collector 13 to permit said electrospun polymer fibers 27 to coat the first surface 21 of said three-dimensional object 5. A second high voltage power is applied to the electrospinning apparatus 3 generating electrospun polymer fibers 27 that are attracted to the three-dimensional object 5 and coat it with electrospun polymer fibers 27 in three dimensions, as before. This time, however, more nanofibers 27 will be deposited on the second surface 24 of the three-dimensional object 5, to provide a more even coat of nanofibers 27. In some embodiments, the electrically conductive supporter 7 may be reoriented such that it is perpendicular, rather than parallel, to the spinneret 11 and combined with continuous rotation of the object attached to the electrically conductive supporter 7. Rotation of the object 5 may provide the benefit of evenly coating each of the surfaces.

In some embodiments, a significant amount of time may be required to produce a single, nanofiber-coated scaffold of relatively small size. Lengthy deposition times may be necessary because the objects must be coated one at a time (i.e. one scaffold was coated and removed before the next could be placed on the needle for coating.) to prevent the possibility of "webs" of nanofibers forming between multiple electrically conductive supporters and objects. Both of these issues may be addressed by altering the electrically conductive supporter 7 arrangement and design. Moreover, utilizing any method which increases the quantity of ions at the surface of the object could decrease the amount of time required to coat the object while preventing problems such as "webs" from forming between multiple electrically conductive supporters 7 or objects 5, as discussed above.

While such an approach that may or may not be desired for a specific application, in some embodiments, aligned fibers could be generated using any one of the may methods known in the art for that purpose including, without limitation, rotating disks or drums or parallel wires.

The method and apparatus of the present invention may be used in a wide variety of applications including without limitation biomedical applications, coating small mechanical or electrical components, filtration applications, and/or combinations thereof. In some embodiments, the method and apparatus of the present invention may be used in biomedical applications including, without limitation, tissue engineering of collagenous and non-collagenous tissues including, bone, cartilage, tendon, ligament, skin, and combinations thereof. The method and apparatus of the present invention are not, however, limited to poorly conductive scaffolds or tissue-engineering applications. In some embodiments, for example, small, complex electronic components may be provided a hydrophobic nanofiber coating to allow air to pass through for cooling purposes while maintaining a barrier to prevent direct contact with water. In fact, it is believed that such an embodiment of the present invention could produce electrical components capable of being completely submerged in water to facilitate more efficient heat transfer, or "water-cooled", in a fashion similar to modern internal-combustion engines. In some embodiments, the method and apparatus of the present invention may be used to coat scaffolds used for filtration with accurate and complete three-dimensional electrospun coatings. Moreover, it is believed that there are numerous other applications the present invention in areas where current electrospinning technology in two dimensions is utilized.

In light of the foregoing, it should be appreciated that the present invention significantly advances the art by providing a method and apparatus for coating poorly conductive three-dimensional objects with nanofibers that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Example 1

Methods and Materials

Preparation of Nanofiber-Coated Scaffolds

A basic electrospinning apparatus was experimentally adapted with the addition of a single, fine-point needle to the flat plate collector. A 1.0% (w/v) solution of PLLA (700 kDa, Polysciences, Warrington, Pa.) in chloroform (Sigma-Aldrich, St. Louis, Mo.) was prepared and stirred continuously over a 12 hour period. The solution was then loaded into a 5 mL syringe (Luer-Lok tip, BD, Franklin Lakes, N.J.) having a blunt-tip needle (25 gauge, ½ inch in length, BD) attached to it. The syringe was placed into the syringe pump (NE-300, New Era Pump Systems, Farmingdale, N.Y.), and the positive electrode from a high-voltage power supply (ES60-10W, Gamma High Voltage Research, Ormond Beach, Fla.) was connected. A fine (0.5 mm diameter, 35 mm length) stainless steel needle was attached to a flat, grounded collector, and the end of the needle was inserted by hand through each of a number of poorly conductive, pre-formed rectangular-shaped tissue scaffolds (0.6 cm×0.5 cm×0.5 cm in dimensions) composed of PCL/PLLA (75/25). Nanofibers of PLLA were generated and deposited onto the surface of the scaffolds using an applied voltage of 13.1 kV and working distance of 6 cm between the electrospinning tip and the tip of the grounded needle. FIG. 1 is an illustration of the basic arrangement for the electrospinning design utilized in this process.

Scaffold Drying and Immersion in Liquid

Scaffolds were coated in a one-by-one fashion. The time required to coat each scaffold sufficiently ranged from 55 to 70 minutes. Immediately after a scaffold was coated, it was removed carefully from the stainless steel needle without greatly disturbing the nanofibers on its surface. The scaffold was then transferred to a small, covered petri dish and left to dry in a fume hood at ambient temperature (~22° C.) overnight (~14 hours). Dried nanofiber-coated scaffolds were then placed into separate wells of a 12-well culture plate and stored at 4° C. Nanofiber-coated scaffolds were immersed in 100% ethanol for a period of 24 hours.

Nanofiber Morphology

Uncoated and electrospun-coated scaffolds were mounted on copper studs and sputtercoated with silver for examination by scanning electron microscopy (JEOL-7401, Japanese Electron Optics Laboratory, Peabody, Mass.; SEM). The SEM was operated using multiple accelerating voltages (1.0-2.0 kV) and specimen images were recorded and collected digitally.

Results

Figure 4:
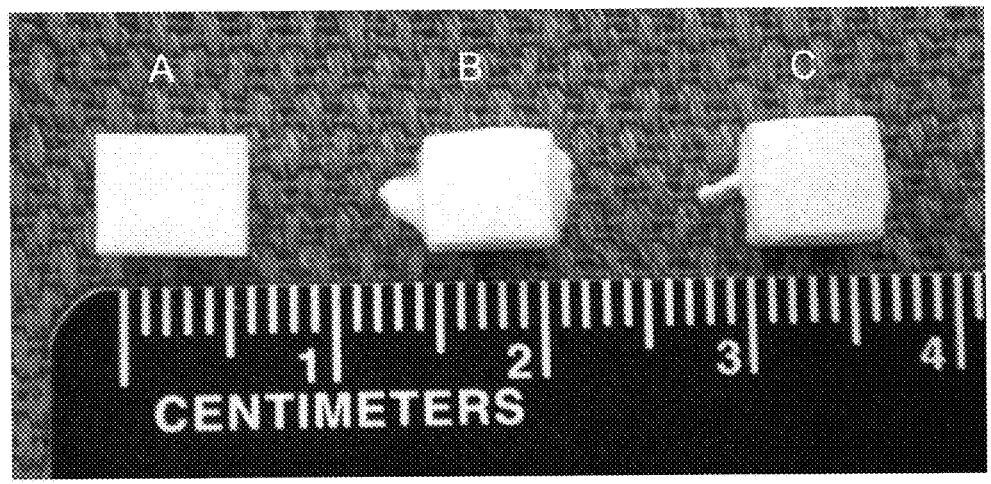
FIG. 4 is photograph comparing an uncoated PCL/PLLA scaffold (4A) and a PLLA nanofiber-coated PCL/PLLA scaffold (4B) and a PLLA nanofiber-coated PCL/PLLA scaffold prepared according to at least one embodiment of the present invention after 24 hour sterilization by immersion in 100% ethanol (4C). The stainless steel needles have been removed from the scaffolds (4B) and (4C) and mounds or "peaks" of electrospun PLLA are left in their place.

FIG. 3 shows a representative specimen mounted onto the end of the fine-point, stainless steel needle. FIG. 4 shows a macroscopic comparison between representative examples of uncoated, coated, and coated/sterilized PCL/PLLA tissue scaffolds. There is a clear difference in size and shape between uncoated (FIG. 4 (left)) and the two nanofiber-coated scaffolds (FIG. 4 (center and right)), these two latter samples being covered and increased in dimensions by PLLA nanofibers electrospun over their surfaces. Electrospinning was accomplished with use of a small stainless steel needle inserted left-to-right through the two relevant scaffolds shown in the FIG. 4. The small, irregular surface features visible on coated scaffolds (FIG. 4 (center and right)) are the direct result of initial PLLA nanofiber deposition at the tip of the needle during the electrospinning process. Additionally, the coated scaffold (FIG. 4 (right) demonstrates that electrospun PLLA nanofibers remain attached to the underlying scaffold after 24 hours of exposure to 100% ethanol.

Figure 5:
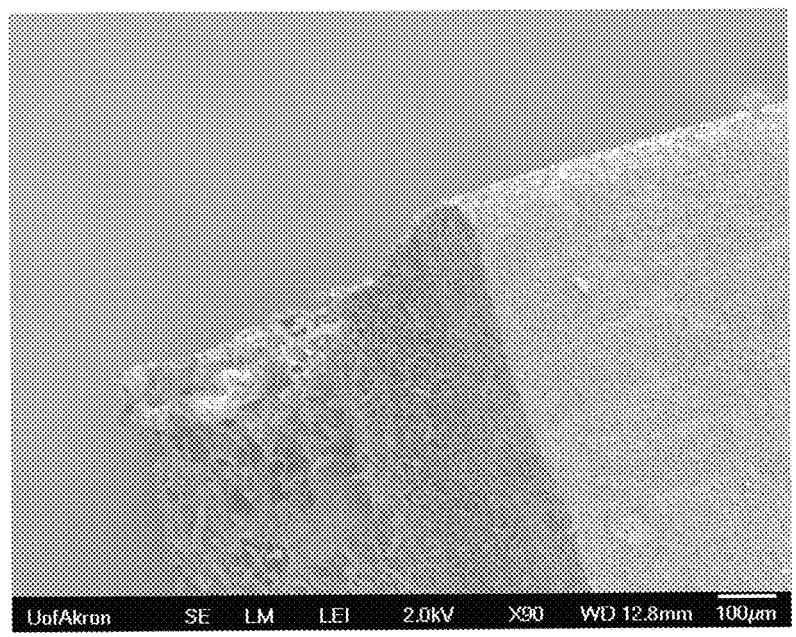
FIG. 5 is a Scanning Electron Microscope (SEM) image of a corner of a representative rectangular-shaped, porous PCL/PLLA (75/25) scaffold uncoated by electrospun nanofibers.

FIG. 5 illustrates the structure of the PCL/PLLA scaffold having no nanofibers covering its surface. The scaffold is porous, and its surface features are readily distinguishable on SEM from the features of a scaffold coated with electrospun PLLA nanofibers.

For ease of explanation, all six surfaces or sides of the rectangular scaffolds coated with nanofibers are labeled A-F in SEM images presented. (FIGS. 6-9). The needle was inserted through the scaffold surfaces A and F. Letters designate the following: A—the "top" or surface of a scaffold that faced the electrospinning tip, B through E—the four scaffold surfaces parallel to the inserted needle, and F—the "bottom" or surface of a scaffold facing away and physically hidden from the electrospinning tip.

Figure 6A:
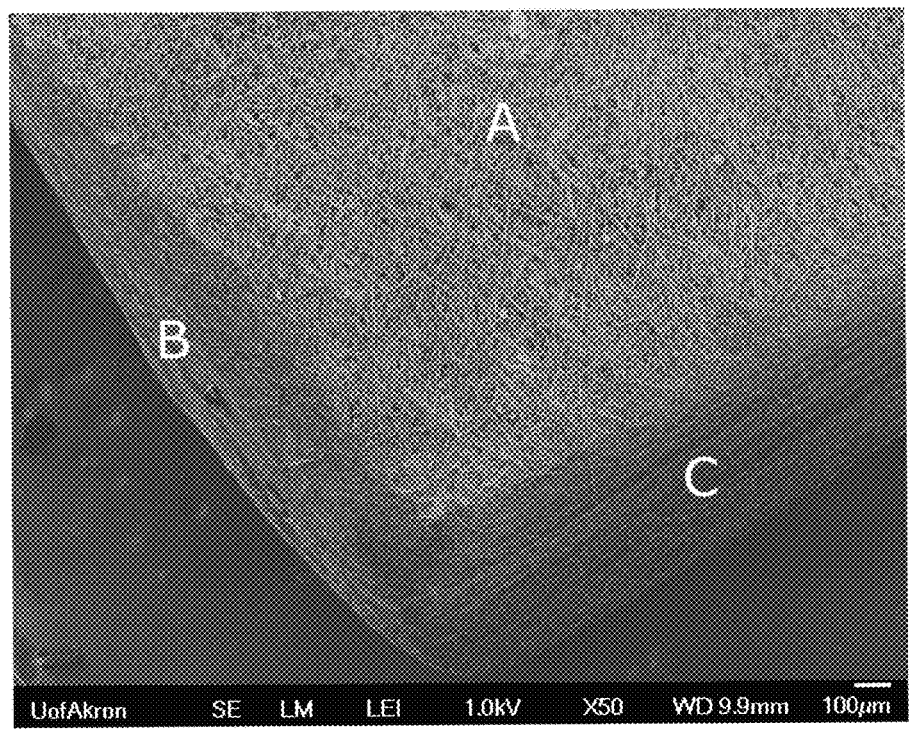
FIGS. 6A and 6B are SEM images showing aspects of the six nanofiber-coated surfaces of a rectangular-shaped PCL/PLLA specimen into which a stainless steel needle has been inserted through its opposing A and F surfaces and the specimen coated with nanofibers according to at least one embodiment of the present invention. All six surfaces of the object are coated with PLLA nanofibers.
Figure 6B:
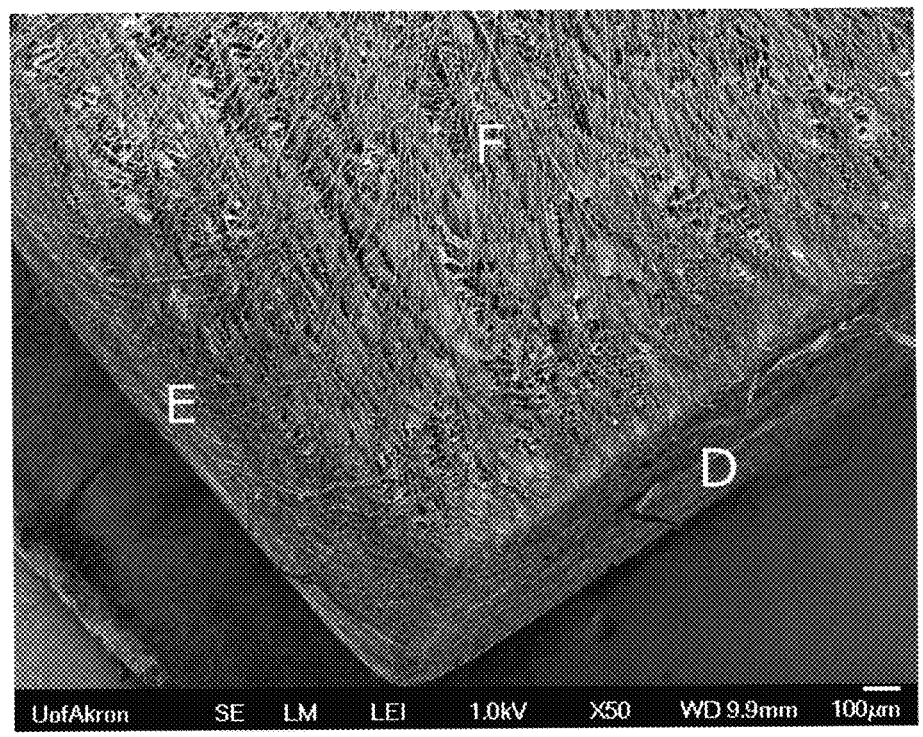
Figure 7:
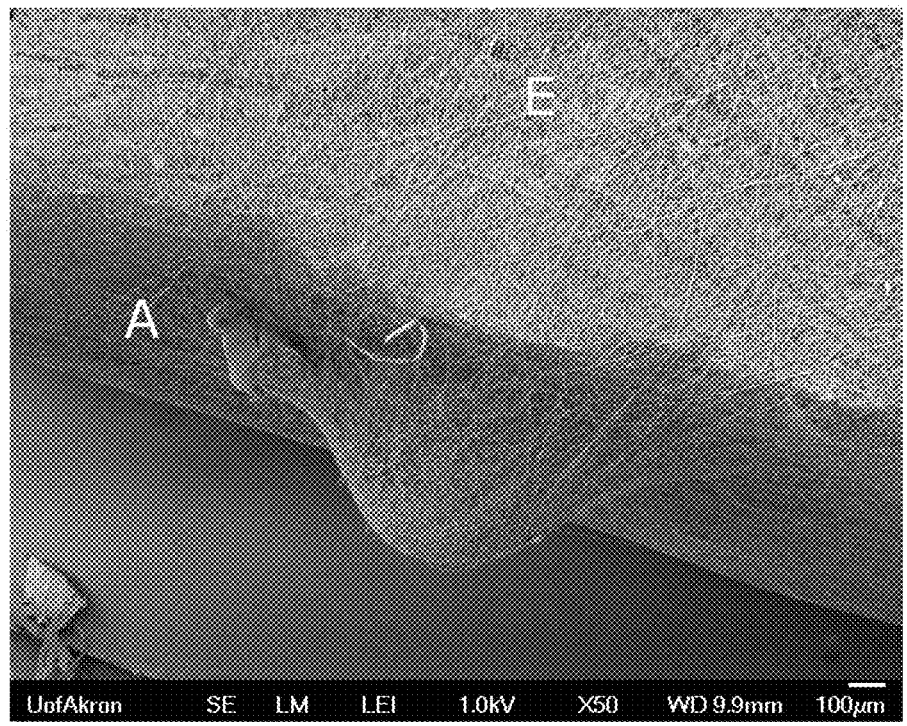
FIG. 7 is an SEM image of a rectangular-shaped PCL/PLLA scaffold coated with nanofibers according at least one embodiment of the present invention, showing the "peak" of PLLA nanofibers which formed at the tip of the needle protruding from top surface (A) of a rectangular-shaped PCL/PLLA scaffold.
Figure 8:
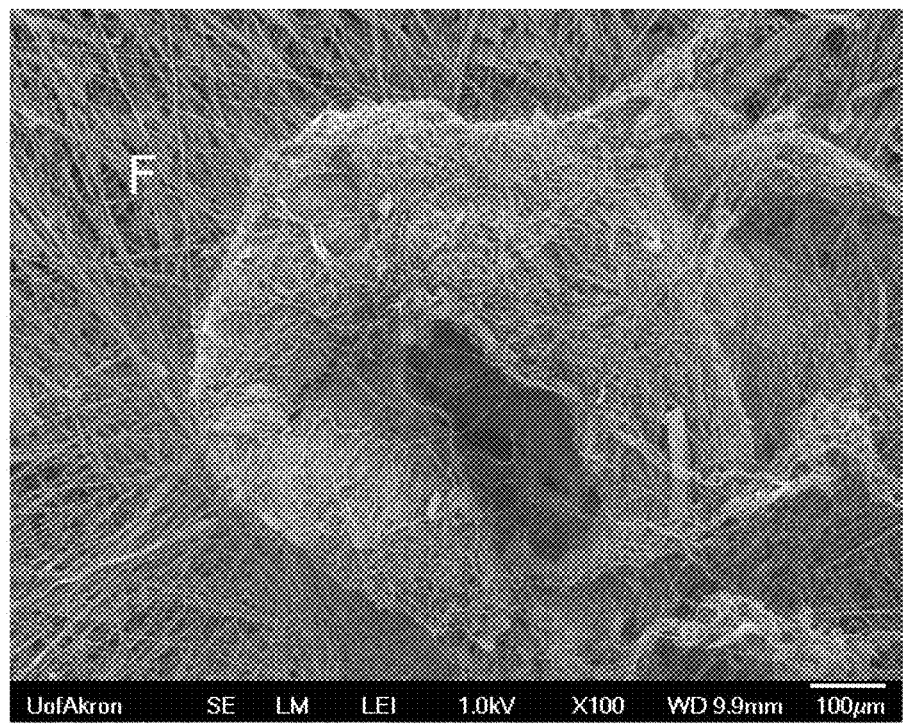
FIG. 8 is an SEM image of a rectangular-shaped PCL/PLLA scaffold coated with nanofibers according at least one embodiment of the present invention depicting the bottom surface (F) of a representative PLLA-electrospun PCL/PLLA scaffold through which a stainless steel needle had been inserted. The area in the immediate center of the image field is the location of needle insertion and is devoid of nanofibers. Collection of nanofibers about the surface center is the result of nanofibers deposited directly onto the stainless steel needle.

FIG. 6 shows nanofiber coverage over all six surfaces of the electrospun scaffolds. The image of FIG. 6A demonstrates complete coverage on the top (A) and two separate surfaces (B and C) of the scaffold. FIG. 6B illustrates coverage over the other two surfaces (D and E) as well as the scaffold bottom (F). FIG. 7 presents an image of the "peak" of PLLA nanofibers formed over scaffold surface A as a result of the stainless steel needle protruding from this scaffold side facing the electrospinning tip. The F scaffold surface, opposing the A scaffold surface of the specimen, is visible in FIG. 8. The grouping of nanofibers around the central portion of this image demonstrates the collection of PLLA around the point of protrusion of the metal needle at this surface.

Figure 9:
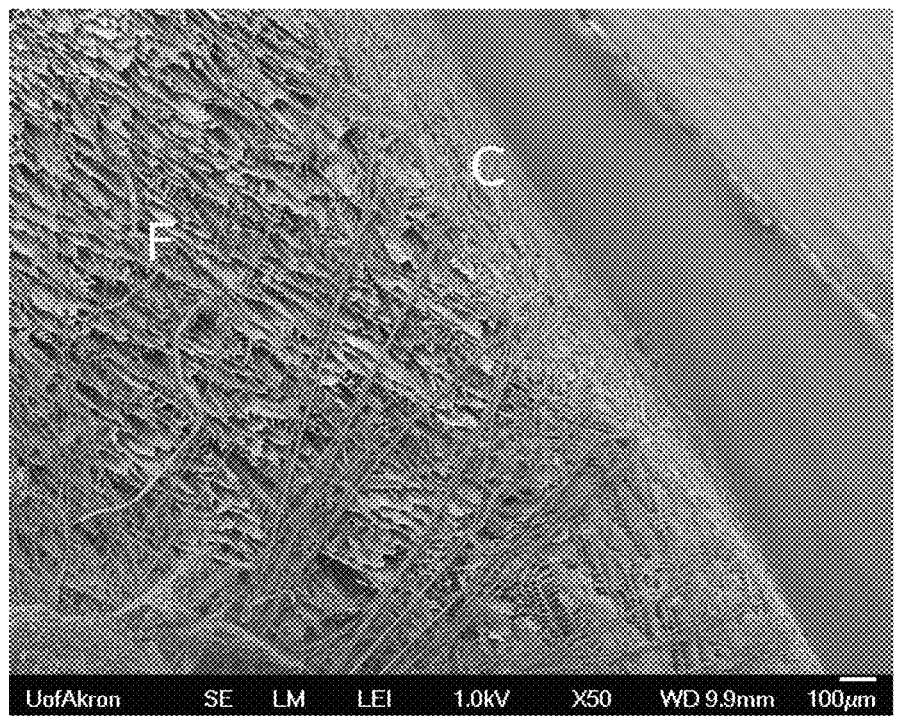
FIG. 9 is an SEM image of a rectangular-shaped PCL/PLLA scaffold coated with nanofibers according at least one embodiment of the present invention showing incomplete coverage of PLLA nanofibers on the bottom surface (F) of a needle-inserted PCL/PLLA scaffold which faced away from and was hidden from the tip of the electrospinning unit.
Figure 10:
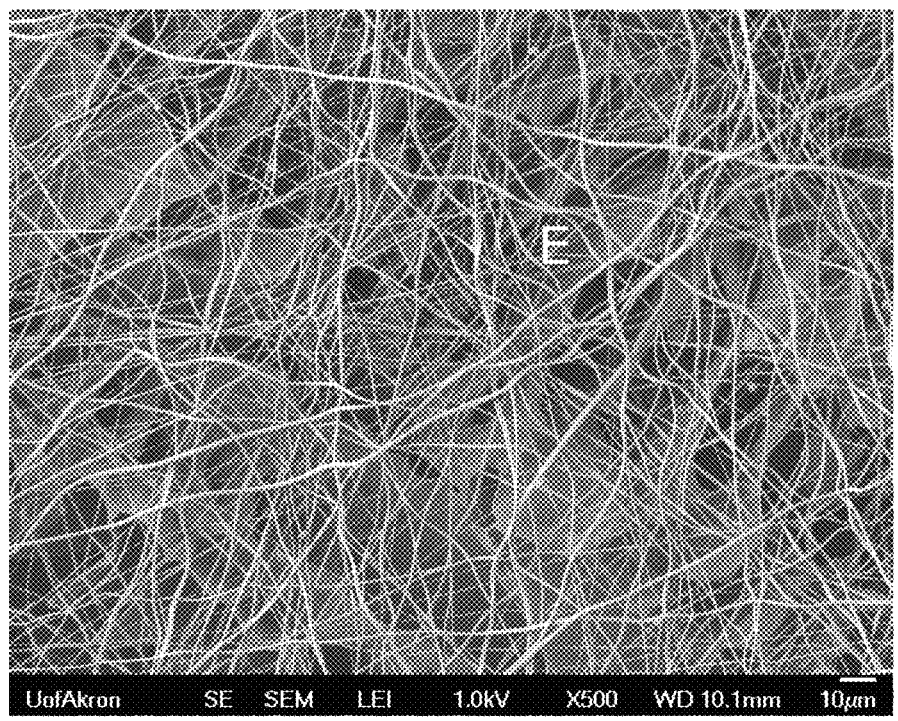
FIG. 10 is an enlargement of an SEM image of a rectangular-shaped PCL/PLLA scaffold coated with nanofibers according at least one embodiment of the present invention showing PLLA nanofibers on a surface E of a needle-inserted PCL/PLLA scaffold. In this example, extended nanofibers are randomly arranged and generally uniform in diameter. The electrospun coating over the surface is relatively sparse and portions of the open, porous PCL/PLLA scaffold are visible beneath the nanofibers.

FIG. 9 shows incomplete coverage of nanofibers on the F surface of a specimen as well as illustrating the edge between surfaces F and C where the nanofibers are in close contact with the scaffold. Nanofibers of PLLA are visible in the foreground of FIG. 10. The underlying PCL/PLLA scaffold is seen through the gaps between individual fibers on a surface E when utilizing higher magnification in the SEM.

What is claimed is:

1. A method for coating an object in three dimensions with electrospun polymer nanofibers, comprising:
   a) placing a three-dimensional object between a spinneret and a grounded collector, the spinneret holding a spinnable polymer fluid and the three-dimensional object having a first surface oriented toward the spinneret and a second surface oriented toward the grounded collector;
   b) mounting the three-dimensional object on an electrically conductive supporter by passing it through the interior of the three-dimensional object such that a first end of the electrically conductive supporter extends through the first surface of the three-dimensional object and a second end of the electrically conductive supporter is electrically connecting to the grounded collector; and
   c) applying a voltage to the spinneret that is sufficient to generate electrospun polymer fibers of said spinnable polymer fluid that are attracted to said three-dimensional object and coat said three-dimensional object with electrospun polymer fibers in three dimensions.

2. The method of claim 1 further comprising providing a gap between the second surface of said three-dimensional object and said grounded collector, such that in said step (c) the electrospun polymer fibers coat the second surface of the three-dimensional object.

3. The method of claim 1, wherein said step (b) includes mounting the three-dimensional object to at least a second electrically conductive supporter, said second electrically conductive supporter passing it through the interior of the three-dimensional object such that a first end of the second electrically conductive supporter extends through the first surface of the three-dimensional object and a second end of the second electrically conductive supporter is electrically connecting to the grounded collector.

4. The method of claim 1 wherein the supporter has a higher conductivity than the three-dimensional object.

5. The method according to claim 1, wherein the three-dimensional object is poorly conductive.

6. The method according to claim 1, wherein the three-dimensional object is a subcellular, cellular, tissue, or organ scaffold comprised of a polymer selected from the group consisting of biodegradable polyesters, polylactic acid, polycaprolactone, polyglycolic acid, and combinations thereof.

7. The method according to claim 1, wherein said spinnable polymer fluid comprises a polymer selected from the group consisting of polylactic acid, polycaprolactone, polyglycolic acid, collagen, chitosan, fibrinogen, and combinations thereof.

8. The method according to claim 1, wherein said spinnable polymer fluid comprises poly L-lactic acid.

9. The method according to claim 1, wherein said electrically conductive supporter is comprised of a highly conductive material selected from the group consisting of stainless steel, titanium, copper, gold, silver aluminum, iron, and combinations thereof.

10. The method according to claim 1, wherein said electrically conductive supporter is a stainless steel needle.

11. The method according to claim 1 further comprising:
   d) after said step (c), inverting said three-dimensional object and said conductive supporter so that said second surface of said three-dimensional object and said second end of said electrically conductive supporter are oriented toward said spinneret and said first surface of said three-dimensional object and said first end of said electrically conductive supporter are oriented toward said grounded collector wherein there is a gap between the first surface of said three-dimensional object and said grounded collector to permit said electrospun polymer fibers to coat the first surface of said three-dimensional object;
   e) electrically connecting said first end of said electrically conductive supporter to said grounded collector; and
   f) applying a second high voltage power to said spinneret thereby generating electrospun polymer fibers of said spinnable polymer fluid that are attracted to said three-dimensional object and coat said three-dimensional object with electrospun polymer fibers in three dimensions.

* * * * *